United States Patent
Sato et al.

(10) Patent No.: US 7,238,504 B2
(45) Date of Patent: Jul. 3, 2007

(54) PROCESS FOR PREPARING AN IMMOBILIZED ENZYME

(75) Inventors: Manabu Sato, Kamisu-machi (JP); Masami Shimizu, Kamisu-machi (JP); Minoru Kase, Kamisu-machi (JP); Takaaki Watanabe, Kamisu-machi (JP); Jun Kohori, Tokyo (JP)

(73) Assignee: Kao Corporation, Tokyo (JP)

( * ) Notice: Subject to any disclaimer, the term of this patent is extended or adjusted under 35 U.S.C. 154(b) by 52 days.

(21) Appl. No.: 10/609,401

(22) Filed: Jul. 1, 2003

(65) Prior Publication Data

US 2005/0019883 A1  Jan. 27, 2005

(30) Foreign Application Priority Data

Jul. 2, 2002  (JP) .............................. 2002-192974

(51) Int. Cl.
*C12N 11/00* (2006.01)

(52) U.S. Cl. ...................................... 435/174; 435/134

(58) Field of Classification Search ................ 435/134, 435/135, 174, 180
See application file for complete search history.

(56) References Cited

U.S. PATENT DOCUMENTS

| | | | |
|---|---|---|---|
| 5,177,013 A | | 1/1993 | Usui et al. |
| 5,569,594 A | * | 10/1996 | Ikuta et al. .................. 435/134 |
| 5,658,769 A | * | 8/1997 | Bosley et al. ................ 435/135 |
| 6,258,575 B1 | * | 7/2001 | Shimizu et al. .............. 435/134 |
| 6,716,610 B2 | * | 4/2004 | Shimizu et al. .............. 435/134 |
| 2003/0096383 A1 | * | 5/2003 | Shimizu et al. .............. 435/134 |

FOREIGN PATENT DOCUMENTS

| | | | |
|---|---|---|---|
| EP | 322213 A2 | * | 6/1989 |
| EP | 1 008 647 | | 6/2000 |
| EP | 1008647 A2 | * | 6/2000 |
| JP | 62-134090 | | 6/1987 |
| JP | 2000-166589 | | 6/2000 |

OTHER PUBLICATIONS

Ruthven, D.R. editor, Encyclopedia of Separation Technology, vol. 2, John Wiley & Sons, Inc., 1997, p. 1072.*
U.S. Appl. No. 09/453,078, filed Dec. 2, 1999, Shimizu et al.
P. Villeneuve, et al., Journal of Molecular Catalysis B: Enzymatic, vol. 9, No. 4-6, pp. 113-148, "Customizing Lipases for Biocatalysis: A Survey of Chemical, Physical and Molecular Biological Approaches", 2000.
U.S. Appl. No. 11/270,497, filed Nov. 10, 2005, Sato et al.

* cited by examiner

*Primary Examiner*—Leon B. Lankford, Jr.
*Assistant Examiner*—Susan E. Fernandez
(74) *Attorney, Agent, or Firm*—Oblon, Spivak, McClelland, Maier & Neustadt, P.C.

(57) ABSTRACT

Provided is a process for preparing an immobilized enzyme, which comprises the steps of immobilizing an enzyme used for decomposing oil & fat on a carrier, by adsorption, without drying, bringing the immobilized enzyme into contact with a fatty acid triglyceride or fatty acid partial glyceride, or mixtures thereof, and adjusting the moisture content of the enzyme to 5% to 50% by weight based on the weight of the carrier, wherein the enzyme is used for esterification.

10 Claims, No Drawings

PROCESS FOR PREPARING AN IMMOBILIZED ENZYME

FIELD OF INVENTION

The present invention relates to a process for preparing an immobilized enzyme showing a high activity. Such immobilized enzyme is used as a catalyst in the esterification of a fatty acid with an alcohol or transesterification of oil & fat (mono-, di- or triglyceride).

BACKGROUND OF THE INVENTION

The use of an enzyme for decomposing oil and fat, for substituting an acyl group in an ester of a fatty acid and alcohol and in oil & fat (mono-, di- or triglyceride) to produce a new glyceride, is increasing. In particular, when producing oil & fat having a specific functionality, a lipase having a position specificity is used in many cases. In order to recover and reuse the lipase enzyme, an immobilized enzyme can be used.

Many of the immobilized enzymes which are available at present are offered in a dried form such as Lipozyme RM IM®, Lipozyme TL IM® and Novozym 435® which are marketed by Novozymes Co., Ltd. The dry form is used, taking into consideration the inhibition of an enzyme from deactivation during storing and proper handling. However, deactivation of an adsorbed immobilized enzyme is liable to occur at a step where the immobilized enzyme is dried under a reduced pressure, in a vacuum or by heating, and the maximum activity shown during adsorption is not achieved in many cases in actually displaying such activity.

A method has been proposed in which an enzyme is adsorbed and immobilized on a carrier, thereby forming an immobilized enzyme, and then immediately brought into direct contact with a reaction substrate without drying to carry out esterification (Japanese Patent Application Laid-Open No. 166589/2000). According to this method, the reaction is delayed in the first reaction by virtue of the influence of a large amount of moisture contained in the immobilized enzyme, but a high activity can be achieved on and after the second reaction. However, the immobilized enzyme has to be immediately contacted with a reaction substrate, because it is not suitable for storage as an immobilized enzyme. Also proposed is a method in which an immobilized enzyme is dried in contact with a fatty acid derivative to thereby enhance development of its activity (Japanese Patent Application Laid-Open No. 134090/1987). In this method, however, the immobilized enzyme has to be slowly dried, and thus its efficiency is inferior. In addition thereto, it is complicated to set up the conditions thereof, and expensive facilities are required. Accordingly, it is not practical.

SUMMARY OF THE INVENTION

The present invention provides a process for preparing an immobilized enzyme which comprises the steps of immobilizing an enzyme used for decomposing oil & fat on a carrier by adsorption, without drying, bringing the immobilized enzyme into contact with a fatty acid triglyceride, a fatty acid partial glyceride, or mixtures thereof, and adjusting the moisture content of the immobilized enzyme to 5% to 50% by weight based on the weight of the carrier, wherein the enzyme is used for esterification.

Furthermore, the present invention provides a process for preparing an immobilized enzyme which comprises the steps of immobilizing an enzyme used for decomposing oil & fat on a carrier by adsorption, without directly drying, by bringing the immobilized enzyme into contact with a fatty acid, fatty acid triglyceride, fatty acid partial glyceride, or mixtures thereof, in an amount of 20% to 3000% by weight, based on the weight of the carrier, thereby dehydrating the immobilized enzyme, wherein the moisture content of the immobilized enzyme is 1% to 50% by weight based on the weight of the carrier, wherein the enzyme is used for esterification.

DETAILED DESCRIPTION OF THE INVENTION

All references cited are hereby incorporated by reference.

The process of the present invention described above makes it possible to control the moisture content of the immobilized enzyme without drying, which brings about deactivation of an immobilized enzyme, thereby producing an immobilized enzyme for esterification having a high activity. Without wanting to be limited by theory, it is considered that the deactivation of an enzyme used for decomposing oil & fat which is brought about when the enzyme is dried to obtain an immobilized enzyme results from damage (for example, breakage of a higher order structure such as conformation) exerted on the enzyme by forcibly removing moisture by drying. Accordingly, the present invention relates to a process for preparing an immobilized enzyme for esterification (including transesterification) having a high activity by controlling the moisture content of an immobilized enzyme without drying which brings about deactivation of an enzyme. The present inventors have succeeded in inhibiting deactivation of an enzyme when producing an immobilized enzyme for esterification to give a high activity by controlling the remaining moisture content of the immobilized enzyme using the process described above.

The carrier for the immobilized enzyme used in the present invention includes inorganic carriers such as celite, diatomaceous earth, kaolinite, silica gel, molecular sieves, porous glass, activated carbon, calcium carbonate and ceramics and organic polymers such as ceramics powder, polyvinyl alcohol, polypropylene, chitosan, ion exchange resins, hydrophobic adsorption resins, chelating resins and synthetic adsorption resins, wherein ion exchange resins are particularly preferred.

The ion exchange resins are preferably porous anion exchange resins. Such porous carrier has a large surface area and therefore can adsorb an enzyme in a larger amount. The resin has preferably a particle diameter of 100 to 1000 μm and a pore diameter of 10 to 150 nm. The material therefor includes a phenol-formaldehyde base, a polystyrene base, an acrylamide base and a divinylbenzene base, wherein a phenol-formaldehyde base resin (for example, Duolite A-568 manufactured by Rohm and Hass Co., Ltd.) is particularly preferred.

The enzyme used for decomposing oil & fat used in the present invention is preferably a lipase. Commercial lipases from microorganisms as well as lipases from animals and plants can be used. Lipases from microorganisms include those from a *Rizopus* genus, an *Aspergillus* genus, a *Mucor* genus, a *Pseudomonas* genus, a *Geotrichum* genus, a *Penicillium* genus and a *Candida* genus. Particularly when a functional oil and fat is to be produced, preferably used lipases are from a *Rizopus* genus, an *Aspergillus* genus, a *Mucor* genus, a *Pseudomonas* genus, a *Geotrichum* genus and a *Penicillium* genus which are 1,3-position selective lipases having a position specificity capable of selectively forming a bond in an intended position of glycerol.

When immobilizing these enzymes, the enzymes may be adsorbed directly on the carrier, but the carrier may be treated in advance with a fat-soluble fatty acid or a derivative thereof before adsorbing thereon the enzymes in order to obtain such absorbtion state that high activity is revealed. The fat-soluble fatty acid which may be used includes saturated or unsaturated, linear or branched fatty acids which have 8 to 18 carbon atoms and which may be substituted with a hydroxyl group. Specifically, it includes capric acid, lauric acid, myristic acid, oleic acid, linoleic acid, α-linolenic acid, ricinolic acid and isostearic acid. The derivatives thereof include esters of these fatty acids with monohydric or polyhydric alcohols, phospholipids and derivatives obtained by adding ethylene oxide to these esters. Specifically, the derivatives include methyl esters, ethyl esters, monoglycerides, diglycerides, ethylene oxide adducts, polyglycerin esters, sorbitan esters and sucrose eaters of the fatty acids described above. These fat-soluble fatty acids or the derivatives thereof may be used in combination of two or more thereof.

With respect to a method for bringing these fat-soluble fatty acids or the derivatives thereof into contact with the carrier, the fat-soluble fatty acids or the derivatives thereof may be added directly to water or an organic solvent, or they may be once dispersed and dissolved in an organic solvent in order to improve dispersibility and then added to the carrier dispersed in water. The preferred organic solvent includes chloroform, hexane and ethanol. The amount of the fat-soluble fatty acids or the derivatives thereof used therein is preferably 1 to 500%, particularly 10 to 200% by weight based on the weight of the carrier. The contact temperature is preferably 0 to 100° C., more preferably 20 to 60° C., and the contact time is preferably approximately 5 minutes to 5 hours. The carrier after this treatment may be filtered, recovered, and, if necessary, dried. The drying temperature is preferably from room temperature to 100° C., and drying may be effected under reduced pressure.

The preferred temperature for immobilizing the enzyme can be determined according to the characteristics of the enzyme, and is preferably 0 to 60° C., more preferably 5 to 40° C. at which the enzyme is not deactivated. The pH of an enzyme solution used in immobilization may fall in a range where the enzyme is not denatured and can be determined according to the characteristics of the enzyme as is the case with the temperature. The pH is preferably 3 to 9. A buffer solution may be used in order to maintain the pH range, and the buffer solution includes an acetic acid buffer solution, a phosphoric acid buffer solution and a tris hydrochloric acid buffer solution.

An enzyme concentration in the enzyme solution described above is preferably not higher than the solubility at saturation but a sufficient concentration in view of immobilization efficiency. Further, it is also possible to use a supernatant obtained by removing insoluble matters from the enzyme solution by centrifugal separation and a solution obtained by purifying the enzyme solution by ultrafiltration. The amount of the enzyme to be used is preferably 5 to 1000%, more preferably 10 to 500% by weight based on the weight of the carrier.

In the present invention, the enzyme used for decomposing oil & fat is preferably immobilized on the carrier by adsorption and then, without drying, treatment (A): brought into contact with a fatty acid triglyceride, fatty acid partial glyceride, or mixtures or treatment (B): dehydrated while contacting with a fatty acid, fatty acid triglyceride, fatty acid partial glyceride, or mixtures whereby the remaining moisture content of the immobilized enzyme is controlled. In the present invention, the term "without drying" means "without subjecting to drying under reduced pressure, vacuum or heating".

The remaining moisture content is adjusted to 5 to 50% by weight, preferably 15 to 50% by weight in the case of treatment (A). In the case of treatment (B), it is adjusted to 1 to 50% by weight, preferably 1 to 30% by weight.

As examples of fatty acid triglyceride or fatty acid partial glyceride which is brought into contact with the immobilized enzyme in the moisture content-controlling treatment (A), materials which can be used include vegetative liquid fats & oils such as rapeseed oil, soybean oil and sunflower oil, fish oils such as sardine oil, tuna oil and skipjack oil, marine animal oils such as whale oil, monoglycerides and diglycerides derived therefrom, mixtures thereof and transesterified fats & oils obtained from these fats & oils. Combinations of two or more thereof may be used. In the moisture content-controlling treatment (B), in addition to the fatty acid triglycerides or fatty acid partial glycerides described above, fatty acids produced from these compounds can be used as well. Fatty acids used in treatment (B) are preferably fatty acids produced from vegetable liquid fats & oils such as rapeseed oil, soybean oil and sunflower oil and fish oils such as sardine oil, tuna oil and skipjack oil. Fatty acids, fatty acid triglycerides or fatty acid partial glycerides used in treatment (A) or treatment (B) are preferably selected from oil phase substrates used in actual esterification or transesterification using the immobilized enzyme prepared by the process of the present invention.

The amount of a fatty acid glyceride used in treatment (A) is preferably 500 to 5000%, more preferably 800 to 4000% and even more preferably 1000 to 3000% by weight based on the weight of the carrier from the viewpoint of sufficient contact with the immobilized enzyme and avoiding wastes due to excess use thereof. When the remaining moisture content may be 15 to 50% by weight based on the weight of the carrier, the amount of a fatty acid glyceride to be used is preferably 500 to 3000%, more preferably 800 to 2500% based on the weight of the carrier, and when the remaining moisture content is reduced to 5 to 15% based on the weight of the carrier, the amount of fatty acid glyceride to be used is preferably 2000 to 5000%, more preferably 2500 to 4000% based on the weight of the carrier. Further, the amount of fatty acid or fatty acid glyceride used in treatment (B) is preferably 20 to 3000%, more preferably 100 to 1000% based on the weight of the carrier from the same viewpoints as described above and from the viewpoints of enhancing the fluidity and improving the dehydration efficiency.

A method for bringing the immobilized enzyme into contact with a fatty acid glyceride in the treatment (A) may be any one of dipping, stirring and allowing a fatty acid glyceride to flow through a column filled with the immobilized enzyme by means of a pump. The contact temperature does not matter as long as the oil phase does not solidify during contact, and it can suitably be determined according to the characteristics of the fatty acid glyceride used and the characteristics of the enzyme. However, it is preferably 5 to 60° C., more preferably from room temperature to 40° C. The contact time is suitably 0.1 to 72 hours, and a longer contact time may be taken or the immobilized enzyme may be stored in contact with a fatty acid glyceride. When dehydration is carried out while the immobilized enzyme is in contact with a fatty acid or fatty acid glyceride in treatment (B), the dehydration temperature is the same as the case of treatment (A), and the dehydration time is suitably 0.5 to 24 hours. In the case of treatment (B), however, dehydration can be quickly carried out, and the dehydration step can be completed in a short time by setting the moisture reduction rate per hour to 50% or more, preferably 60% or more and more preferably 70% or more. Publicly known methods such as a method using a dehydrating agent such as molecular sieves and a method of treating under reduced pressure can be used as the dehydration method. Considering that use of the dehydrating agent requires operation of removing the dehydrating agent after the treatment, treatment under reduced pressure is preferred.

The moisture content of the immobilized enzyme upon adsorbing and immobilizing the enzyme on the carrier falls usually in the range of from 120 to 200% based on the weight of the carrier, and the remaining moisture content can be reduced to 5 to 50% based on the weight of the carrier by (A) bringing the immobilized enzyme into contact with a fatty acid glyceride. When dehydration is carried out while (B) bringing the immobilized enzyme into contact with a fatty acid or fatty acid glyceride, the remaining moisture content can be reduced down to 1 to 50% based on the weight of the carrier. The immobilized enzyme is recovered by filtering at a stage where the contact treatment or the dehydration treatment is completed or before using the immobilized enzyme, and it is used in the actual reaction.

Thus, although not wanting to be limited by theory, damage exerted on an enzyme by forcibly removing moisture as is the case with usual drying can be reduced by controlling the moisture content using a fatty acid or fatty acid glyceride. This makes it possible to prepare an immobilized enzyme showing a high activity. It is also considered that the excess moisture is removed from the immobilized enzyme by bringing it into contact with a fatty acid glyceride and that a reaction environment suited to the reaction is formed in the vicinity of the enzyme. Further, the immobilized enzyme in which the moisture content thereof is controlled by a preferred method of the present invention can be stored over a long period of time in any state wherein the immobilized enzyme is separated from the fatty acid glyceride which was brought into contact therewith and the state wherein the immobilized enzyme is in contact with a fatty acid glyceride.

EXAMPLES

Example 1

Duolite A-568 (manufactured by Rohm and Hass Co., Ltd.) (100 g) was stirred in 1L of an N/10 NaOH solution for one hour. After filtering, it was washed with 1L of distilled water, and the pH was equilibrated with 1L of a 500 mM acetic acid buffer solution (pH 5). Then, the pH was equilibrated twice each for two hours (2×2h) with 1L of a 50 mM acetic acid buffer solution (pH 5). The carrier was recovered by filtering, and then substitution with 500 ml of ethanol was carried out for 30 minutes. After filtering, the carrier was brought into contact with 500 mL of an ethanol solution containing 100 g of ricinolic acid for 30 minutes. After filtering, buffer solution substitution with 500 ml of the 50 mM acetic acid buffer solution (pH 5) was carried out four times each for 0.5 hour (4×0.5h). After filtering, the carrier was brought into contact with 1000 ml of a 10% Lilipase™ (manufactured by Nagase Sangyo Co., Ltd.) solution at room temperature for 4 hours for adsorption of the enzyme. After adsorption, the carrier was filtered and washed with 500 ml of the 50 mM acetic acid buffer solution (pH 5) for 0.5 hour. After washing, the immobilized enzyme was recovered by filtering. The immobilized enzyme had a remaining moisture content of 168% based on the weight of the carrier having the enzyme adsorbed thereon.

Rapeseed oil (1000 g) was added to this immobilized enzyme, and the mixture was stirred at 40° C. for 24 hours and then filtered to recover the immobilized enzyme. The immobilized enzyme had a remaining moisture content of 29% based on the weight of the carrier having the enzyme adsorbed thereon.

Eight g of the immobilized enzyme thus obtained was weighed in terms of a dry weight, and a 200 mL four neck flask was charged with it. A mixture (80 g) of oleic acid and glycerol (oleic acid/glycerol=2.0 in terms of a molar ratio) was added thereto to carry out esterification at 40° C. under a reduced pressure of 400 Pa. After the reaction, the reaction liquid was separated from the immobilized enzyme by filtration, and oleic acid and glycerol were charged again in such amounts as to give the above-mentioned mixture and a reaction was carried out. After the reaction, a reaction was carried out once again by the same method. That is, the same immobilized enzyme was used to carry out esterification three times in total.

The glyceride composition of each reaction liquid was analyzed by gas chromatography after subjecting the reaction liquid to trimethylsilylation. The time when the total of diglyceride (DG) and triglyceride (TG) reached 70% is shown in Table 1. The reaction times of the first reaction and the second reaction or thereafter were as short as 1.67 hours and 1.53 hours, respectively, and the activity was high.

Example 2

An enzyme was adsorbed by the same method as in Example 1, washed with a buffer solution and filtered to recover the immobilized enzyme. Rapeseed oil (3000 g) was added to this immobilized enzyme, and the mixture was stirred at 40° C. for 24 hours and then filtered to recover the immobilized enzyme. The immobilized enzyme had a remaining moisture content of 11% based on the weight of the carrier having the enzyme adsorbed thereon.

The immobilized enzyme thus obtained was used to carry out reaction in the same manner as in Example 1. As a result, the reaction times of the first reaction and the second reaction or thereafter were as short as 1.69 hours and 1.52 hours, respectively, and the activity was high.

Example 3

An enzyme was adsorbed by the same method as in Example 1, washed with a buffer solution and filtered to recover the immobilized enzyme. Oleic acid (400 g) was added to this immobilized enzyme, and the mixture was stirred at 40° C. under a reduced pressure of 400 Pa for 0.5 hour and then filtered to recover the immobilized enzyme. The immobilized enzyme had a remaining moisture content of 31% based on the weight of the carrier having the enzyme adsorbed thereon.

The immobilized enzyme thus obtained was used to carry out a reaction in the same manner as in Example 1. As a result, the reaction times of the first reaction and the second reaction or thereafter were as short as 1.63 hours and 1.58 hours, respectively, and the activity was high.

Example 4

An enzyme was adsorbed by the same method as in Example 1, washed with a buffer solution and filtered to recover the immobilized enzyme. Oleic acid (400 g) was added to this immobilized enzyme, and the mixture was stirred at 40° C. under a reduced pressure of 400 Pa for 18 hours and then filtered to recover the immobilized enzyme.

The immobilized enzyme had a remaining moisture content of 2.4% based on the weight of the carrier having the enzyme adsorbed thereon.

The immobilized enzyme thus obtained was used to carry out a reaction in the same manner as in Example 1. As a result, the reaction times of the first reaction and the second reaction or thereafter were 1.45 hours and 1.43 hours, respectively, and were sufficiently short even in the first reaction, and the activity was high.

Comparative Example 1

An enzyme was adsorbed by the same method as in Example 1, washed with a buffer solution and filtered to recover the immobilized enzyme. At this time, the immobilized enzyme had a remaining moisture content of 178% based on the weight of the carrier. This immobilized enzyme was dried as it was at 40° C. under a reduced pressure of 100 Pa for 24 hours. The immobilized enzyme after drying had a remaining moisture content of 3% based on the weight of the carrier having the enzyme adsorbed thereon.

The immobilized enzyme thus obtained was used to carry out a reaction in the same manner as in Example 1. As a result, the reaction times of the first reaction and the second reaction or thereafter were as notably long as 2.27 hours and 2.23 hours, respectively, and the esterification activity was inferior to those in Examples 1 to 4.

Comparative Example 2

An enzyme was adsorbed by the same method as in Example 1, washed with a buffer solution and filtered to recover the immobilized enzyme. At this time, the immobilized enzyme had a remaining moisture content of 178% based on the weight of the carrier.

The immobilized enzyme thus obtained was used to carry out a reaction in the same manner as in Example 1. As a result, the reaction times of the first reaction and the second reaction or thereafter were 3.52 hours and 1.88 hours, respectively. The reaction was sufficiently rapid and the activity was high in the second reaction and thereafter. However, the reaction in the first reaction was slow compared with those in Examples 1 to 4.

What is claimed is:

1. A process for preparing a treated immobilized enzyme, which comprises the sequential steps of:
   i) immobilizing an enzyme used for decomposing oil and fat on a carrier by adsorption,
   ii) without directly drying, bringing the immobilized enzyme from step i) into contact with a composition consisting essentially of at least one of a fatty acid, a fatty acid triglyceride, a fatty acid partial glyceride, or mixtures thereof in an amount of 20% to 3000% by weight, based on the weight of the carrier, and
   iii) dehydrating the immobilized enzyme, wherein the moisture content of the immobilized enzyme is 1% to 50% by weight based on the weight of the carrier.

2. The process for preparing an immobilized enzyme as defined in claim 1, wherein the fatty acid, fatty acid triglyceride or fatty acid partial glyceride which is brought into contact with the immobilized enzyme is an oil phase substrate of the enzyme.

3. The process of claim 1, wherein dehydrating is by at least one method selected from the group consisting of using molecular sieves and treating under reduced pressure.

4. The process of claim 1, further comprising storing said immobilized enzyme after dehydrating.

5. The process of claim 1, wherein said enzyme is a lipase.

6. The process of claim 1, wherein said carrier is treated in advance with a fat-soluble fatty acid or a derivative thereof before adsorption with said enzyme.

7. The process of claim 1, wherein the amount of enzyme is 5 to 1,000 wt. % based on the weight of said carrier.

8. The process of claim 1 wherein the moisture content of the immobilized enzyme as a result of contacting in step ii)

TABLE 1

| | Remaining moisture after washing with buffer solution (based on carrier weight) | Moisture content-reducing treatment conditions | | | | Remaining moisture after moisture content-reducing treatment (based on carrier weight) | DG + TG = 70% reaching time | | |
|---|---|---|---|---|---|---|---|---|---|
| | | Fatty acid or fat & oil (based on carrier weight) | Temperature | Treatment time | Treatment pressure | | First reaction | Second reaction | Third reaction |
| Example 1 | 168% | 1000% rapeseed oil | 40° C. | 24 hours | Normal pressure | 29% | 1.67 hr | 1.53 hr | 1.53 hr |
| Example 2 | 168% | 3000% rapeseed oil | 40° C. | 24 hours | Normal pressure | 11% | 1.69 hr | 1.52 hr | 1.52 hr |
| Example 3 | 168% | 400% oleic acid | 40° C. | 0.5 hour | 400 Pa | 31% | 1.63 hr | 1.58 hr | 1.58 hr |
| Example 4 | 168% | 400% oleic acid | 40° C. | 18 hours | 400 Pa | 2.4% | 1.45 hr | 1.43 hr | 1.43 hr |
| Comparative Example 1 | 178% | — | 40° C. | 24 hours | 100 Pa | 3% | 2.27 hr | 2.23 hr | 2.23 hr |
| Comparative Example 2 | 178% | — | — | — | — | — | 3.52 hr | 1.88 hr | 1.88 hr | is from 1 to 30% by weight, based on the weight of the carrier.

9. The process of claim 1, wherein the amount of fatty acid, fatty acid triglyceride, fatty acid partial glyceride or mixture thereof is from 100 to 1,000% by weight, based on the weight of the carrier.

10. The process of claim 1, wherein the moisture content of said immobilized enzyme after step i) is 120 to 200 wt. %, based on the weight of the carrier.

* * * * *